(12) United States Patent
Jin et al.

(10) Patent No.: US 9,808,606 B2
(45) Date of Patent: Nov. 7, 2017

(54) VALVE SYSTEM FOR INFLATABLE MEDICAL DEVICE

(71) Applicant: ConvaTec Technologies Inc., Las Vegas, NV (US)

(72) Inventors: Yun Jin, Bridgewater, NJ (US); Christopher Carter Gregory, Newtown, PA (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 0 days.

(21) Appl. No.: 14/745,312

(22) Filed: Jun. 19, 2015

(65) Prior Publication Data
US 2015/0283361 A1    Oct. 8, 2015
US 2017/0259046 A9    Sep. 14, 2017

Related U.S. Application Data

(63) Continuation of application No. 14/000,384, filed as application No. PCT/US2012/025420 on Feb. 16, 2012, now Pat. No. 9,072,875.
(Continued)

(51) Int. Cl.
*A61M 25/10* (2013.01)
*A61M 39/26* (2006.01)
(Continued)

(52) U.S. Cl.
CPC ..... *A61M 25/10186* (2013.11); *A61F 5/4405* (2013.01); *A61M 5/3134* (2013.01);
(Continued)

(58) Field of Classification Search
CPC ...... A61M 39/24; A61M 39/26; A61M 39/22; A61M 25/1025; A61M 25/10186;
(Continued)

(56) References Cited

U.S. PATENT DOCUMENTS 851,530 A    4/1907    Edward
2,254,997 A    9/1941    Fisher
(Continued)

FOREIGN PATENT DOCUMENTS

CN    105407961 A    3/2016
JP    S58-501012 A    6/1983
(Continued)

OTHER PUBLICATIONS

Merriam-Webster Dictionary definition for "integrated". Available online Feb. 1, 2016 at http://www.merriam-webster.com/dictionary/integrated.*
(Continued)

*Primary Examiner* — Kevin C Sirmons
*Assistant Examiner* — Amber Stiles
(74) *Attorney, Agent, or Firm* — Wilson Sonsini Goodrich & Rosati (57) ABSTRACT

The present invention relates to a valve system for an inflatable portion of an indwelling medical device and more particularly to a valve system for fluid regulation of a catheter comprising a fluid inflatable portion that undergoes pressure changes within the body during use.

20 Claims, 3 Drawing Sheets

Related U.S. Application Data (60) Provisional application No. 61/443,884, filed on Feb. 17, 2011.

(51) Int. Cl.
*A61M 39/24* (2006.01)
*A61M 39/22* (2006.01)
*A61F 5/44* (2006.01)
*A61M 5/31* (2006.01)

(52) U.S. Cl.
CPC .... *A61M 25/1018* (2013.01); *A61M 25/1036* (2013.01); *A61M 25/10182* (2013.11); *A61M 25/10184* (2013.11); *A61M 39/22* (2013.01); *A61M 39/24* (2013.01); *A61M 39/26* (2013.01); *A61M 2039/2473* (2013.01); *A61M 2039/2493* (2013.01); *Y10T 29/49826* (2015.01)

(58) Field of Classification Search
CPC ........ A61M 25/1018; A61M 25/10182; A61M 25/10184; A61M 25/1036; A61M 5/3134; A61M 2039/2493; A61M 2039/2473; A61F 5/4405
USPC .......... 604/99.01–99.04, 212, 245–247, 249
See application file for complete search history.

(56) References Cited

U.S. PATENT DOCUMENTS

| | | | |
|---|---|---|---|
| 3,127,148 | A | 3/1964 | Collar |
| 3,211,150 | A | 10/1965 | Foderick |
| 3,446,245 | A | 5/1969 | Clifford, Jr. |
| 3,721,726 | A | 3/1973 | Schwartzman |
| 3,777,757 | A | 12/1973 | Gray et al. |
| 4,116,201 | A | 9/1978 | Shah |
| 4,178,938 | A | 12/1979 | Au |
| 4,280,498 | A | 7/1981 | Jensen |
| 4,431,019 | A | 2/1984 | Kopp et al. |
| 4,629,159 | A | 12/1986 | Wellenstam |
| 4,948,092 | A | 8/1990 | Kasper et al. |
| 4,949,092 | A | 8/1990 | Crail et al. |
| 5,350,364 | A | 9/1994 | Stephens et al. |
| 5,454,784 | A | 10/1995 | Atkinson et al. |
| 5,496,300 | A | 3/1996 | Hirsch et al. |
| 5,957,151 | A | 9/1999 | Dalcourt et al. |
| 6,050,973 | A | 4/2000 | Duffy |
| 6,146,374 | A | 11/2000 | Erskine et al. |
| 7,727,188 | B2 | 6/2010 | Machado et al. |
| 8,016,816 | B2 | 9/2011 | Gregory |
| 8,052,671 | B2 | 11/2011 | Christensen et al. |
| 8,888,739 | B2 | 11/2014 | Gregory et al. |
| 2003/0079752 | A1 | 5/2003 | Hart et al. |
| 2003/0229259 | A1 | 12/2003 | Waksman et al. |
| 2004/0010238 | A1 | 1/2004 | Manera et al. |
| 2004/0039374 | A1 | 2/2004 | Tighe et al. |
| 2004/0158197 | A1 | 8/2004 | Bellhouse et al. |
| 2004/0176703 | A1 | 9/2004 | Christensen et al. |
| 2005/0082828 | A1 | 4/2005 | Wicks et al. |
| 2005/0101939 | A1 | 5/2005 | Mitchell |
| 2005/0124932 | A1 | 6/2005 | Foster et al. |
| 2005/0256460 | A1* | 11/2005 | Rome ................ A61M 39/26 604/247 |
| 2005/0273083 | A1 | 12/2005 | Lebel et al. |
| 2008/0009794 | A1* | 1/2008 | Bagaoisan ......... A61B 17/0057 604/104 |
| 2008/0103463 | A1 | 5/2008 | Tsai et al. |
| 2008/0114316 | A1 | 5/2008 | Christensen et al. |
| 2008/0147012 | A1 | 6/2008 | Rome |
| 2008/0175719 | A1 | 7/2008 | Tracey et al. |
| 2009/0163892 | A1 | 6/2009 | McMichael et al. |
| 2010/0191192 | A1 | 7/2010 | Prasad et al. |
| 2010/0217189 | A1 | 8/2010 | Pepper |
| 2013/0030387 | A1 | 1/2013 | Williams et al. |
| 2014/0107572 | A1 | 4/2014 | Jin et al. |
| 2016/0339227 | A1 | 11/2016 | Tsai et al. |

FOREIGN PATENT DOCUMENTS

| | | |
|---|---|---|
| WO | WO-8300070 A1 | 1/1983 |
| WO | WO-2004045704 A2 | 6/2004 |
| WO | WO-2011100187 A1 | 8/2011 |
| WO | WO-2013074763 A1 | 5/2013 |
| WO | WO-2013109293 A1 | 7/2013 |
| WO | WO-2015017646 A1 | 2/2015 |
| WO | WO-2016187350 A1 | 11/2016 |

OTHER PUBLICATIONS

PCT Patent Application No. PCT/US2012/025420 International Preliminary Report on Patentability issued Aug. 21, 2013.
PCT Patent Application No. PCT/US2012/025420 International Search Report and Written Opinion completed Jun. 6, 2012.
European Patent Application No. 12849279.0 Communication dated Mar. 23, 2016.
PCT/US2012/065239 International Preliminary Report on Patentability issued May 20, 2014.
PCT/US2012/065239 International Search Report completed Mar. 8, 2013.
PCT/US2012/065239 Written Opinion completed Mar. 8, 2013.
PCT/US2014/049115 International Preliminary Report on Patentability mailed Feb. 11, 2016.
PCT/US2014/049115 International Search Report completed Oct. 28, 2014.
PCT/US2014/049115 Written Opinion completed Oct. 28, 2014.
ROC (Taiwan) Patent Application No. 101142959 Office Action dated Mar. 21, 2016.
U.S. Appl. No. 13/877,890 Office Action dated Mar. 27, 2014.
U.S. Appl. No. 14/000,384 Office Action dated Sep. 11, 2014.
U.S. Appl. No. 14/341,647 Office Action dated May 5, 2016.
U.S. Appl. No. 14/449,035 Office Action dated Feb. 12, 2016.
U.S. Appl. No. 14/745,312 Office Action dated Feb. 17, 2016.
U.S. Appl. No. 14/449,035 Office Action dated Sep. 14, 2016.
Chinese Patent Application No. 201280067212.0 Third Office Action dated Feb. 27, 2017 (Summary in English).
European Patent Application No. 14832568.1 Supplementary European Search Report dated Feb. 15, 2017.
Japanese Patent Application No. 2014-542455 Office Action dated Dec. 6, 2016.
New Zealand Patent Application No. 727366 First Examiner's Report dated Jan. 17, 2017.

* cited by examiner

Fig. 1

Fig. 3

VALVE SYSTEM FOR INFLATABLE MEDICAL DEVICE

CROSS-REFERENCE

This application is a continuation application of Ser. No. 14/000,384, filed Aug. 19, 2013, which is a United States National Phase Application of International Application Ser. No. PCT/US2012/25420, filed Feb. 16, 2012, which claims the benefit of and the right of priority to U.S. Patent Application No. 61/443,884 file Feb. 17, 2011, which are incorporated herein by reference in its entirety.

FIELD OF THE INVENTION

The present invention relates to a valve system for an inflatable portion of an indwelling medical device and more particularly to a valve system for fluid regulation of a catheter comprising a fluid inflatable portion that undergoes pressure changes within the body during use. The present invention also relates to methods of treatment using said valve system and indwelling medical devices comprising said valve systems.

BACKGROUND OF THE INVENTION

Indwelling medical devices with inflatable portions include, for example, catheters having urinary, fecal, thoracic and abdominal applications. The inflatable portion of these catheters is typically used for retention and/or sealing.

The present valve system is useful in such devices where there are pressure changes within the inflatable portion in use.

The present valve system is particularly useful in the type of rectal catheter or fecal management system described in U.S. Pat. No. 7,727,188, US 2004/00393748A1 and US 2008/0103463A1 which are incorporated herein by reference.

The catheters used in these fecal management systems rely on a balloon at the proximal end of the catheter to retain and seal the catheter within the body. The balloon is inserted into the body in a deflated condition and is properly positioned on the distal side of the rectal muscle. The balloon is inflated once it is properly positioned. In order to remove the device, the balloon is deflated and withdrawn past the rectal muscle and outside of the body. The balloon is inflated and deflated through one or more passageways. The passageways are accessible through tubing that extends along a catheter so as to be accessible for inflation and deflation when the catheter is properly positioned in the body.

The balloon needs to be properly inflated for retaining and sealing the catheter within the body and properly deflated for insertion into and removal from the body.

It has been discovered that it would also be very desirable if the balloon pressure was self-adjusting in response to pressure changes within the body as might occur during body movement, such as from voluntary or involuntary movement from repositioning the body, coughing, sneezing, peristalsis, eating, etc.

It has been found that known devices, which are unable to self-adjust, may cause trauma to the patient, or be expelled from the body, following pressure changes within the body.

The invention sets out to address these and other problems with the prior art.

SUMMARY OF THE INVENTION

The present invention is a valve system that accomplishes effective inflation and deflation of the inflatable balloon portion of a catheter that is positionable within the body while compensating for pressure changes to the inflatable balloon due to pressure changes to the body.

The purpose of the invention disclosed herein is to provide a simple to use self-regulated system to control the internal pressure within an inflatable medical device so as to prevent excessive pressure on the body due to over-inflation.

In a first aspect, the present invention provides a valve system for an inflatable portion of an indwelling medical device. The valve system preferably comprises a fluid passageway having a one-way valve associated therewith, said one-way valve being movable between an open position and a closed position, said open position permitting fluid to pass through said passageway into the inflatable portion. The valve system may further or alternatively comprise a compensator associated with said passageway, said compensator permitting fluid to enter or leave said passageway in response to pressure changes within said passageway caused by pressure changes in the inflatable portion of the medical device. Preferably, said one-way valve comprises a duckbill valve or an elastomeric disk. Preferably, the fluid is air, water, or saline. Preferably, said compensator includes a porous plug permitting fluid flow there through, preferably in two directions.

With such a system, fluid can be slowly released through the compensator during short episodes of contraction (i.e. less than a few minutes), such as during a cough. Contraction of the body around the inflatable portion is a problem because it causes a conditions equivalent to over inflation of the balloon. Over inflation is a recognized problem because it can cause bruising, tissue necrosis and infection. Conversely, when there is excess space available within the body, fluid is allowed to enter the device's inflatable portion without restriction through the one-way valve, permitting the inflatable portion to expand quickly after a contraction. A failure to expand would lead to conditions equivalent to an under inflation of the inflatable portion of the indwelling medical device. Under inflation may lead to the indwelling medical device being expelled from the body or otherwise not performing its function correctly. It is therefore a key feature of the present invention that it enables the inflatable portion of a medical device to inflate and deflate in response pressure exerted on the inflatable portion by the body.

The present valve system is particularly useful in rectal catheters or fecal management systems, particularly those described in U.S. Pat. No. 7,727,188, US 2004/00393748A1 and US 2008/0103463A1, which are incorporated herein by reference, although it may equally find use in other indwelling medical devices.

In an embodiment, the valve system further comprises a movable seal and a fluid connector associated with said fluid passageway, said movable seal being movable to seal said one-way valve and said compensator while preferably permitting fluid to be added or removed from said fluid passageway through said fluid connector, said seal being positionable to prevent passage of fluid through said fluid connector.

The invention therefore includes a valve system for the inflatable portion of an indwelling medical device comprising: a fluid passageway having a movable one-way valve associated therewith, said one-way valve being movable between an open position and a closed position, said open position permitting fluid to pass through said passageway into the inflatable portion; a compensator associated with said passageway, said compensator permitting fluid to enter or leave said passageway in response to pressure changes within said passageway caused by pressure changes in the inflatable portion of the medical device; and a movable seal with a fluid connector associated with said fluid passageway, said seal being movable to seal said one-way valve and said compensator while permitting fluid to be added or removed from said fluid passageway through said fluid connector, said seal being positionable to prevent passage of fluid through said fluid connector.

In a further embodiment said fluid connector is adapted to receive an attachment member. Typically, attachment of said attachment member to said fluid connector moves said movable seal to seal said one-way valve and said compensator while permitting fluid to be added or removed from said fluid passageway through said fluid connector; whereas removal of said attachment member allows said movable seal to return to its original position and thereby prevent passage of fluid through said fluid connector.

The invention also includes a valve system for an inflatable portion of an indwelling medical device comprising: a fluid passageway; a compensator associated with said fluid passageway, said compensator permitting fluid to enter or leave said fluid passageway in response to pressure changes within said passageway caused by pressure changes in the inflatable portion of the medical device; and a movable seal and a fluid connector associated with said fluid passageway, said movable seal being movable to seal said compensator while permitting fluid to be added or removed from said fluid passageway through said fluid connector, said seal being positionable to prevent passage of fluid through said fluid connector. Preferably, further comprising a one-way valve associated with the fluid passageway, said one-way valve being movable between an open position and a closed position, said open position permitting fluid to pass through said fluid passageway into the inflatable portion. Preferably, wherein said movable seal is movable to seal said compensator and one-way valve simultaneously.

The invention thereby enables the inflatable portion of the indwelling medical device to be inflated or deflated rapidly by way of said attachment member. Preferably the attachment member is a syringe, preferably a Luer tipped syringe. Furthermore, the invention is such that once the device has been inflated, and the attachment member removed, the pressure within the inflatable portion may be regulated by the one-way valve and the compensator of the valve system. When the pressure in the inflatable portion of the medical device is higher than atmospheric pressure, fluid may leave the valve system through the compensator. Whereas, when the pressure in the inflatable portion of the medical device is lower than atmospheric pressure, fluid may enter the valve system through the one-way valve.

In preferred embodiments the movable seal is adapted to move in response to the attachment of an attachment member to the fluid connector, preferably the movable seal comprises an engagement member. Typically, the movable seal moves when the attachment member engages the engagement member.

In preferred embodiments, the movable seal comprises a sealing member and a biasing member. Typically, the biasing member is a spring, preferably a helical spring. Preferably, the valve system comprises a housing and the sealing member comprises a body, a proximal circumferential rib and a distal circumferential rib, wherein, in use, the proximal and distal circumferential ribs provide a fluid tight seal with the housing of the valve system. Preferably, the sealing member comprises at least one aperture for providing fluid communication between a distal face of said sealing member and a proximal face of said sealing member. At least two, three, four, five, six or more apertures may be provided.

Typically, in use, the biasing member biases the sealing member into engagement with an inner wall of the valve system so as to cover said at least one aperture in a substantially fluid tight manner.

In embodiments, the present invention also encompasses a valve system for inflatable portion of an indwelling medical device comprising a fluid connector, a housing, a fluid passageway and a movable seal located within said housing for sealing the fluid connector, wherein the movable seal comprises a sealing member and a biasing member. Preferably, the sealing member comprises at least one aperture for providing fluid communication between a distal face and proximal face of the sealing member. Preferably, when the movable seal seals the fluid connector, the housing of the valve system covers the at least one aperture in a fluid tight manner. Typically, the distal end wall of the housing covers the at least one aperture. Preferably, when uncovered, said at least one aperture provides fluid communication between the fluid connector and the fluid passageway.

In an alternative embodiment, the valve system comprises an activator for opening the one-way valve, preferably by physically engaging therewith. Typically, the activator opens said one-way valve when said activator is activated. Preferably, said activator, when activated, prevents fluid from passing through said compensator. Typically, the one-way valve closes when the activator is deactivated (i.e. released).

The invention therefore provides a valve system for the inflatable portion of an indwelling medical device comprising: a fluid passageway having a movable one-way valve associated therewith, said one-way valve being movable between an open position and a closed position, said open position permitting fluid to pass through said passageway into the inflatable portion; a compensator associated with said passageway, said compensator permitting fluid to enter or leave said passageway in response to pressure changes within said passageway caused by pressure changes in the inflatable portion of the medical device; and an activator for opening the one-way valve.

In embodiments, the valve system further comprises a fluid connector associated with said activator. Preferably, an attachment member for attachment to the fluid connector is provided. Preferably, the activator is activated by applying an axial load thereto. Typically, attachment of said attachment member to said fluid connector activates said activator by applying an axial load to the activator.

In embodiments the activator comprises an activating pin and a biasing member. Typically, the biasing member is a helical spring. Preferably, the activating pin comprises a conduit for providing fluid communication between a distal end and proximal end of said activating pin.

Preferably, the activating pin further comprises a circumferential flange. Typically, the helical spring engages the circumferential flange. Preferably, the activator is activated by applying an axial force to the activator, which, in turn, compresses the helical spring between the circumferential flange and a proximal end wall of the activator chamber, and thereby exposes a proximal portion of the activating pin.

In embodiments when the activating pin does not comprise a conduit, when the activator is deactivated, said circumferential flange may engage with the fluid passageway to provide a fluid tight seal and prevent fluid communication between said one-way valve and said fluid connector. Whereas, when the activator is activated, said circumferential flange disengages with the fluid passageway, providing fluid communication between said one-way valve and said fluid connector. When the activator is deactivated, fluid may also enter or leave the valve system through the compensator.

Typically, the inflatable portion of the medical device may be inflated by passing fluid either through a conduit in the activating pin or by passing said fluid around said circumferential flange.

Preferably, in use, when said attachment member engages said fluid connector, said attachment member further engages a engagement member of the activator and thereby activates said spring activator; typically, by applying an axial force to the activating pin, which compresses the helical spring, and thereby exposes a portion of the central rod or conduit.

Preferably, in use, the one-way valve is opened by the activator. Typically, the activating pin physically engages the one-way valve. Preferably, when the one-way valve is a duck-bill valve, the activating pin engages and opens open the duck-bill valve.

The invention thereby enables the inflatable portion of the indwelling medical device to be inflated or deflated rapidly by way of said attachment member. In all embodiments, preferably the attachment member is a syringe, more preferably a Luer tipped syringe. Preferably the fluid connector has a Luer tip engagement profile. Preferably, the inflatable portion is inflated by the syringe.

Once the device has been inflated, and the attachment member removed, the pressure within the inflatable portion is regulated by the one-way valve and the compensator of the valve system. When the pressure in the inflatable portion of the medical device is higher than atmospheric pressure, fluid will leave the valve system through the compensator. Whereas, when the pressure in the inflatable portion of the medical device is lower than atmospheric pressure, fluid will enter the valve system through the one-way valve.

In all embodiments, the valve system may further include open cell foam in the inflatable portion of the medical device. Preferably, the inflatable portion is foam filled. Preferably, the foam will self-inflate the inflatable portion. This enables the inflatable portion return to its original size following a contraction and expansion cycle within the body e.g. during and following a cough. Suitable foams include polyurethane foams and memory foams.

The activator may be integrated with said fluid passageway or the activator may be separate from said fluid passageway.

A key element of the system is a one-way valve that can be opened through the simple connection of a fluid supply device, such as a syringe, to the fluid passageway. By combining such a one-way valve with an element that allows restricted fluid flow that is blocked by the one-way valve, the desired fluid control can be achieved in a simple to operate form.

In use, the valve systems according to the first aspect of the invention will typically be positioned outside of the body. However, the fluid passageway will typically run from outside of the body to the inflatable portion of the indwelling medical device within the body. Typically, the inflatable portion is a balloon: typically, a balloon which is moulded in its inflated state. Typically, the balloon is filled with an open cell foam. The valve systems of the invention may be incorporated in indwelling medical devices or provided as part of a kit for use with known indwelling medical devices.

In second aspect the invention provides an indwelling medical device, preferably including fecal management systems, particularly those described in U.S. Pat. No. 7,727,188, US 2004/00393748A1 and US 2008/0103463A1, which are incorporated herein by reference; catheters having urinary, fecal, thoracic and abdominal applications; and systems for providing temporary blockage of the colon or ileum, comprising an inflatable portion and any valve system according to the first aspect of the invention.

In a third aspect, the invention provides a method for preparing an inflatable portion of an indwelling medical device for inflation or deflation comprising the steps of:
a) providing a valve system as described in the first aspect of the invention; and
b) attaching an attachment member thereto. Preferably, attachment of the attachment member to the fluid connector enables fluid communication between the attachment member and the inflatable portion of the indwelling medical device.

In a fourth aspect the invention provides a method for inflating the inflatable portion of an indwelling medical device comprising the steps of:
a) preparing an inflatable portion of an indwelling medical device according to the third aspect of the invention; and
b) passing fluid from the attachment member and into said valve system so as to inflate the inflatable portion of the indwelling device.

In a fifth aspect the invention provides a method for deflating the inflatable portion of an indwelling medical device comprising the steps of:
a) preparing an inflatable portion of an indwelling medical device according to the second aspect of the invention; and
b) allowing fluid to flow from the inflatable portion of the indwelling device into the attachment member so as to deflate the inflatable portion of the indwelling device.

In a sixth aspect the invention provides a valve system for an inflatable portion of an indwelling medical device according to the first aspect of the invention for use in the treatment of a patient, preferably by implanting said inflatable portion of said indwelling device in the patient and then typically inflating the inflatable portion.

The first, second, third, fourth, fifth and sixth aspects of the invention, and any embodiments thereof, may combined with one another mutatis mutandis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The above-mentioned and other features and objects of this invention, and the manner of obtaining them, will become more apparent and the invention itself will be better understood by reference to the following description of embodiments of the invention taken in conjunction with the accompanying drawings, wherein.

Although the drawings represent exemplary embodiments of the present invention, the drawings are not necessarily to scale and certain features may be exaggerated to better illustrate and explain the invention. The exemplification set out herein illustrates exemplary embodiments of the invention only.

DETAILED DESCRIPTION OF THE INVENTION

In the present application "proximal" and "distal" are used to refer to "closer to" and "further from" the body or medical device respectively.

Figure 1:
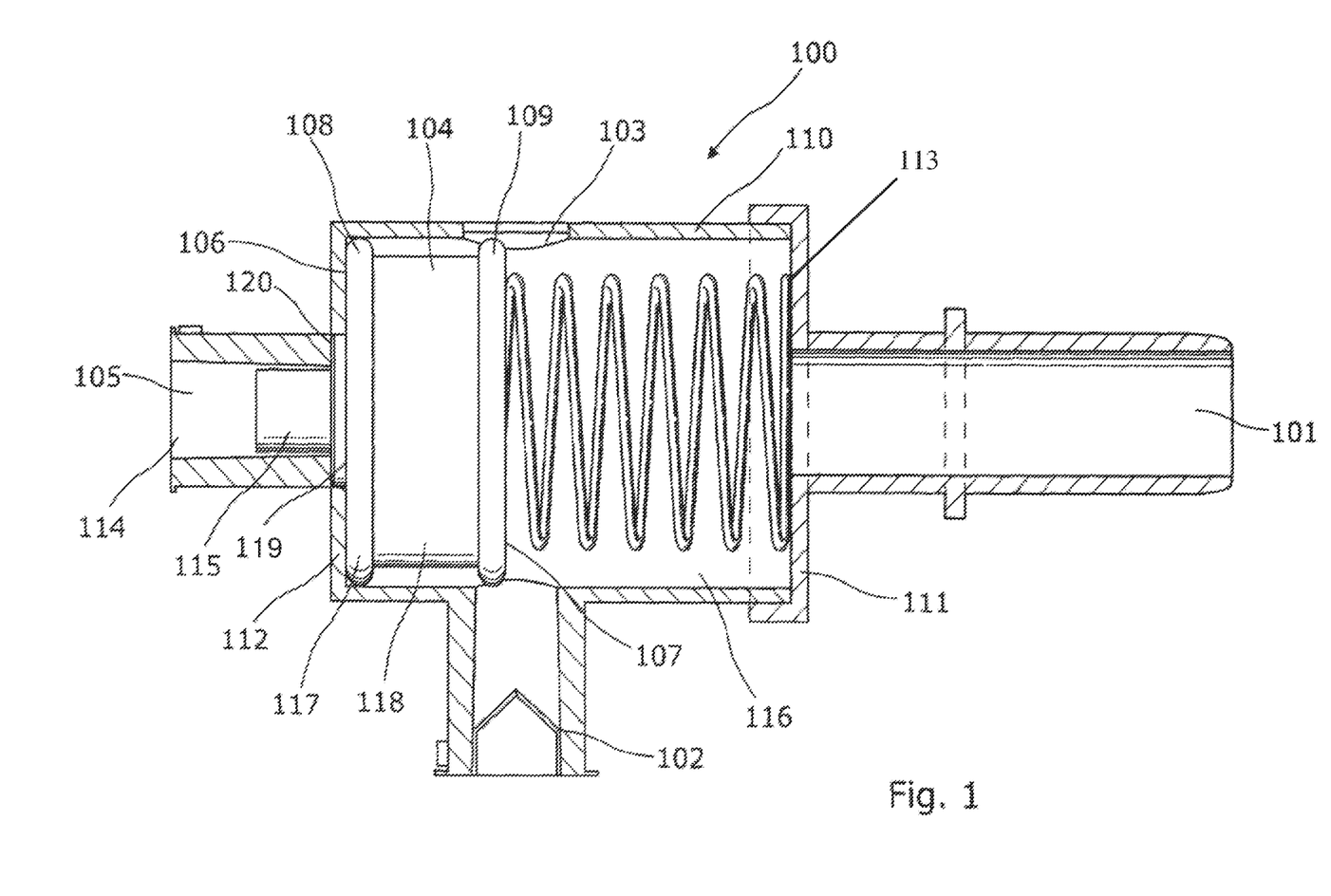
FIG. 1 is a schematic of a valve system according to the invention.

FIG. 1 shows a valve system (100) according to the invention which is suitable for use with an inflatable portion of an indwelling medical device (not shown). The valve system (100) comprises a fluid passageway (101) having a one-way valve (102) associated therewith. The one-way valve (102) is movable between an open position (not shown) and a closed position (shown), said open position permitting fluid to pass through said passageway (101) into the inflatable portion. The valve system (100) further comprises a compensator (103) in association with said passageway (101), said compensator (103) permitting fluid to enter and/or leave said passageway (101) in response to pressure changes (i.e. pressure increases or decreases) within said passageway (101) caused by pressure changes in the inflatable portion of the medical device. The one-way valve (102) is a duckbill valve, although other valve types, such as elastomeric disks, would also be suitable. The one-way valve (102) is orientated so as to allow fluid to enter the valve-system therethrough. The fluid is generally air, although water or saline may also be employed. The compensator (103) includes a porous plug permitting fluid flow therethrough in two directions. The porous plug is made from a porous polymer with a continuous porosity, although other materials may also be used.

Indwelling medical device is intended to include any medical device which is implanted within a human or animal body, preferably including fecal management systems, particularly those described in U.S. Pat. No. 7,727,188, US 2004/00393748A1 and US 2008/0103463A1, which are incorporated herein by reference; catheters having urinary, fecal, thoracic and abdominal applications; and systems for providing temporary blockage of the colon or ileum.

The valve system further comprises a movable seal (104) and a fluid connector (105) associated with said fluid passageway (101), said movable seal (104) being movable to seal said one-way valve (102) and said compensator (103) while permitting fluid to be added or removed from said fluid passageway (101) through said fluid connector (105). As shown, the movable seal (104) is positionable to prevent passage of fluid through said fluid connector (105).

The valve system comprises a housing (110) having a promixal (near the body or inflatable device) end wall (111) and a distal (away from the body or inflatable device) end wall (112). The housing (110) and end walls (111, 112) surround a central chamber (116). The fluid passageway (101) is in fluid communication with the central chamber (116) via an aperture in the proximal end wall (111) and the fluid connector (105) is in fluid communication with the central chamber (116) via an aperture in the distal end wall (112). The compensator (103) and one-way valve (102) are in fluid communication with the central chamber (116), the fluid passageway (101), and the surrounding atmosphere. In the illustrated embodiment, the housing (110) and central chamber (116) are substantially cylindrical, although other non-circular cross-sections are contemplated (e.g. square, hexagonal).

The central chamber (116) of the housing (110) contains the movable seal (104). The movable seal (104) comprises a biasing member (113) and a sealing member (117). In the illustrated embodiment, the biasing member (113) is a helical spring, although other biasing means are also contemplated, such as coil and leaf springs, and flexible polymer members. The helical spring is typically made from a suitable alloy or polymer.

The sealing member (117) comprises cylindrical body portion (118). The cylindrical body portion (118) typically has an outer diameter less than the diameter of the central chamber (116). The sealing member (117) further comprises a proximal face (107) and a proximal circumferential rib (109), and a distal face (106) and a distal circumferential rib (108). The proximal and distal circumferential ribs (109, 108) form a fluid tight seal with the inner surface of the housing (110). Typically, the proximal and distal circumferential ribs (109, 108) have a diameter substantially the same or larger than the diameter of the central chamber (116). The circumferential ribs (108, 109) and the central chamber (116) will generally have substantially the same cross-section. When the housing (110) and central chamber (116) are cylindrical, the sealing member (117), including the circumferential ribs (108, 109) will also have circular cross-sections. If another shape housing is used, complementary cross-sections will be chosen for the circumferential ribs (108, 109), in order to achieve a fluid-tight seal between the movable seal (104) and the housing (110).

The biasing member (113) engages the proximal end wall (111) of the housing (110) and the proximal face (107) of the movable seal (104).

The valve system (100) is shown in its at rest position. In said position, the distal face (106) of the sealing member (117) engages the distal end wall (112) of the housing (110), and the one-way valve (102) and the compensator (103) are in fluid communication with the fluid passageway (101). In said at rest position, fluid may enter the valve system (100) via the one-way valve (102) if the pressure in the inflatable portion of the medical device is lower than atmospheric pressure. In said at rest position, fluid may enter or leave the valve system (100) via the compensator (103) if the pressure in the inflatable portion of the medical device is lower or higher than atmospheric pressure respectively. As such, the valve system (100) can regulate the pressure in the inflatable portion of the medical device.

The movable seal (104) further comprises at least one aperture (not shown in FIG. 1; see 207, 217, and 236 in FIG. 2a, FIG. 2b and FIG. 2c respectively) for providing fluid communication between the distal face (106) and the proximal face (107) of the sealing member (117). In the at rest position, the distal face (106) of the sealing member (117) engages the distal end wall (112) of the housing (110) and distal end wall (112) covers the at least one aperture so as to provide a fluid-tight seal. This distal face (106) of the sealing member (117) further comprises a circular sealing rim (119) which engages with a corresponding trench (120) in the distal end wall (112) of the housing (110) of the valve system (100).

The movable seal (104) further comprises an engagement member (115). The fluid connector (105) is typically in the form of a conduit, typically a tubular conduit (114). The engagement member (115) is typically in the form of a cylindrical protrusion. Typically, the diameter of the engagement member (115) is less than the inner diameter of the tubular conduit (114).

In the illustrated embodiment, the fluid connector (105) is adapted to receive an attachment member (not shown). In use, attachment of the attachment member activates the valve system (100). Typically, the attachment member engages the engagement member (115) and thereby moves the movable seal (104) to seal the one-way valve (102) and the compensator (103), while, at the same time, exposing the at least one aperture (not shown) in the movable seal (104) to provide fluid communication between the fluid connector (105) and the fluid passageway (101). In so doing, the biasing member (113) is acted against, which, in the illustrated embodiment, means that the helical spring is compressed. When the valve system (100) is activated, fluid may be passed from the attachment member to the inflatable portion of the medical device. When the valve system is activated, fluid cannot escape through or enter through the compensator (103) and/or the one-way valve (102) because they are sealed by the movable seal (104). Typically, when the valve system (100) is activated, the proximal and distal circumferential ribs (108, 109) straddle the compensator (103) and the one-way valve (102), and, because the central cylindrical portion (118) of the sealing member (117) is less than that of the circumferential ribs (108, 109), a channel is provided between said compensator (103) and said one-way valve (102).

Removal of the attachment member allows said movable seal (104) to return to its original position under the action of biasing member (113). Once in the at rest position, passage of fluid through said fluid connector (105) is prevented.

The invention thereby enables the inflatable portion of the indwelling medical device to be inflated or deflated rapidly by way of said attachment member. Preferably the attachment member is a syringe, preferably a Luer tipped syringe. Furthermore, the invention is such that once the device has been inflated, and the attachment member removed, the pressure within the inflatable portion of the medical device may be regulated by the one-way valve (102) and the compensator (103) of the valve system (100). When the pressure in the inflatable portion of the medical device is higher than atmospheric pressure, fluid may leave the valve system through the compensator (103). Whereas, when the pressure in the inflatable portion of the medical device is lower than atmospheric pressure, fluid may enter the valve system through the one-way valve (102) and/or the compensator (103).

The sealing member will be typically made from a rubber or silicone. The housing will be typically made from a suitable polymer, such as polypropylene, or silicone. Similar materials may be used for the fluid connector, the proximal and distal end walls, and the fluid passageway. All of which could be selected by the skilled person according to their required function.

Figures 2A, 2B:
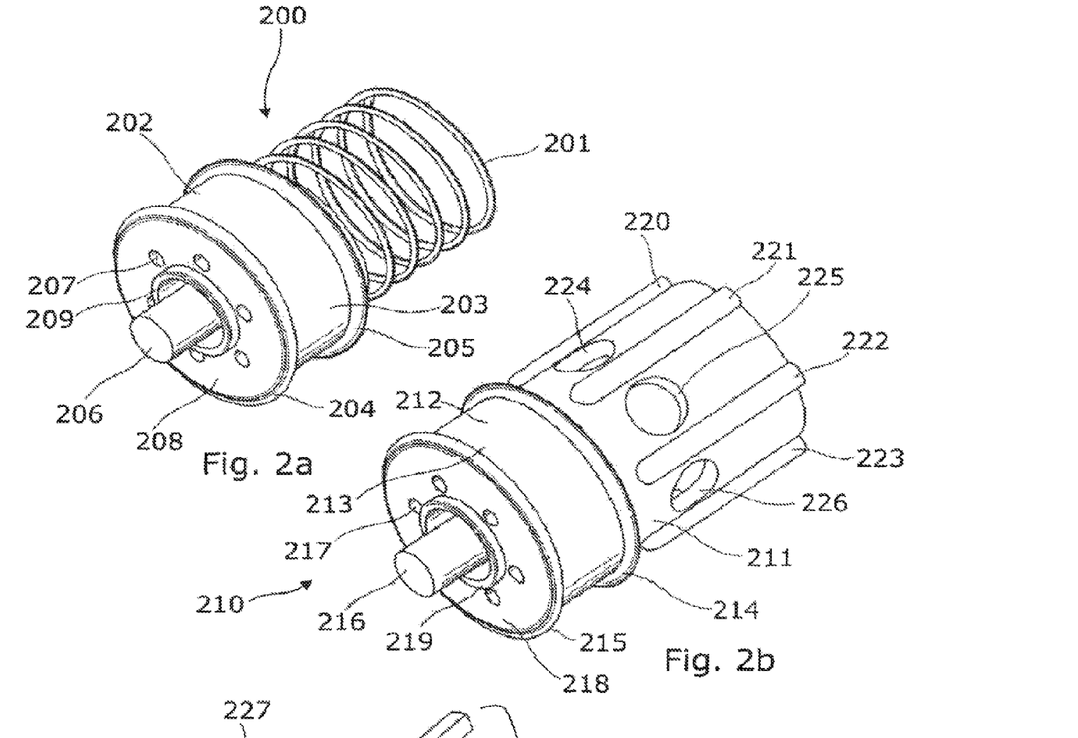
FIG. 2a, FIG. 2b and FIG. 2c are schematics of alternative movable seals.
Figure 2C:
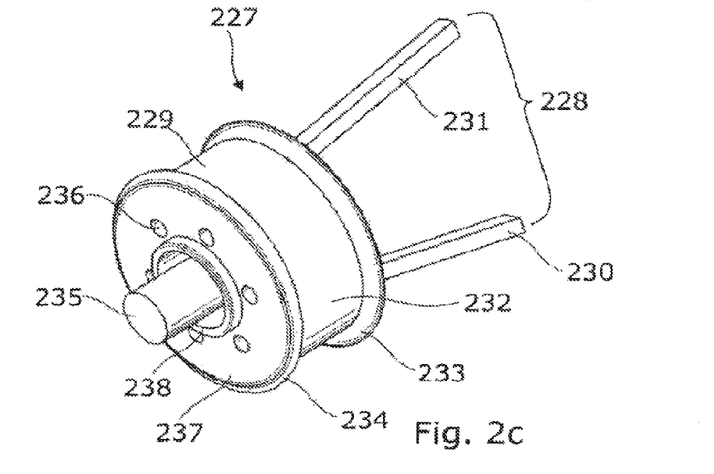

FIGS. 2a, 2b and 2c show alternative embodiments of the movable seal.

FIG. 2a shows a perspective view of the movable seal used in FIG. 1. The movable seal (200) comprises a biasing member (201) and a sealing member (202). The biasing member (201) comprises a helical spring. The helical spring may be made from a suitable alloy or polymer. The sealing member is made from a suitable rubber or silicone. The sealing member (202) comprises a central cylindrical portion (203) and proximal and distal circumferential ribs (204, 205). The movable seal (200) further comprises an engagement member (206) in the form of cylindrical protrusion.

The movable seal (200) additionally comprises at least one aperture (207) for providing fluid communication between the distal face (208) and proximal face (not shown) of the sealing member (202). Six apertures are shown, although more or less may also be used. The distal face (208) of the sealing member (202) further comprises a circular sealing rim (209) which engages with a corresponding trench in the distal end wall of the housing of the valve system.

FIG. 2b provides a perspective view of an alternative movable seal (210). The movable seal (210) comprises a biasing member (211) and a sealing member (212). The biasing member (211) comprises a cylindrical body with parallel, circumferentially spaced ribs (220-223) with interspaced apertures (224-226). The biasing member (211) may be made from a suitable polymer. The sealing member is made from a suitable rubber or silicone. In use, the biasing member (201) biases the movable seal towards the distal end wall of the housing of the valve system. The sealing member (212) comprises a central cylindrical portion (213) and proximal and distal circumferential ribs (214, 215). The movable seal (210) further comprises an engagement member (216) in the form of cylindrical protrusion.

The movable seal (210) additionally comprises at least one aperture (217) for providing fluid communication between the distal face (218) and proximal face (not shown) of the sealing member (212). Six apertures are shown, although more or less may also be used. The distal face (218) of the sealing member (212) further comprises a circular sealing rim (219) which engages with a corresponding trench in the distal end wall of the housing of the valve system.

FIG. 2c provides a perspective view of a further alternative movable seal (227). The movable seal (227) comprises a biasing member (228) and a sealing member (229). The biasing member (228) comprises two flexible legs (230, 231). The biasing member (228) may be made from a suitable polymer. In use, the biasing member (228) biases the movable seal (227) towards the distal end wall of the housing of the valve system. The sealing member (229) is made from a suitable rubber or silicone. The sealing member (229) comprises a central cylindrical portion (232) and proximal and distal circumferential ribs (233, 234). The movable seal (227) further comprises an engagement member (235) in the form of cylindrical protrusion.

The movable seal (227) additionally comprises at least one aperture (236) for providing fluid communication between the distal face (235) and proximal face (not shown) of the sealing member (229). Six apertures are shown, although more or less may also be used. The distal face (237) of the sealing member (229) further comprises a circular sealing rim (238) which engages with a corresponding trench in the distal end wall of the housing of the valve system.

Figure 3:
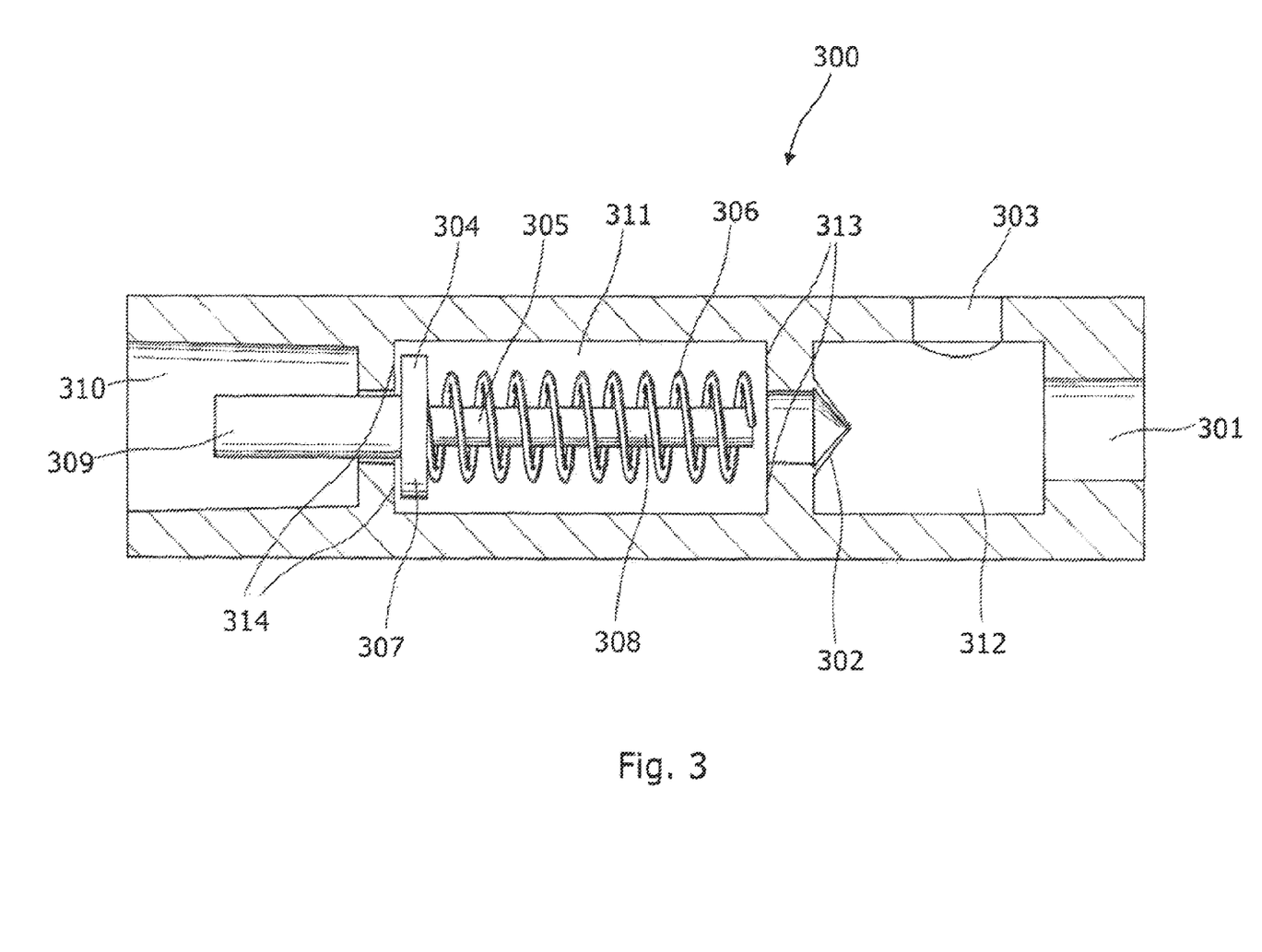
FIG. 3 is a schematic of an alternative valve system according to the invention.

FIG. 3 shows an alternative embodiment of the valve system of the invention which is suitable for use with an inflatable portion of an indwelling medical device (not shown). The valve system (300) comprises a fluid passageway (301) having a one-way valve (302) associated therewith. The one-way valve (302) is movable between an open position (not shown) and a closed position (shown), said open position permitting fluid to pass through said passageway (301) into the inflatable portion of the medical device. The valve system (300) further comprises a compensator (303) in association with said fluid passageway (301), said compensator (303) permitting fluid to enter and/or leave said fluid passageway (301) in response to pressure changes (i.e. pressure increases or decreases) within said passageway (301) caused by pressure changes in the inflatable portion of the medical device. The one-way valve (302) is a duckbill valve, although other valve types, such as elastomeric disks, would also be suitable. The one-way valve (302) is orientated so as to allow fluid to enter the valve-system therethrough. The fluid is generally air, although water or saline may also be employed. The compensator (303) includes a porous plug permitting fluid flow therethrough in two directions. The porous plug is made from aporous polymer, although other materials may also be employed. Typically, the porous polymer has a continuous porosity or is an open-cell foam. Polyurethane foams may be employed.

The valve system (300) comprises an activator (304) for opening the one-way valve (302). The activator (304) opens said one-way valve (303) when said activator (304) is activated. The activator (304) opens the one-way valve (302) by physically engaging therewith (not shown). Preferably, said activator (304), when activated, prevents fluid from passing through said compensator (303). Typically, the one-way valve (302) closes when the activator (304) is disengaged therefrom.

The activator (304) comprises an activating pin (305) and a biasing member (306). Typically, the activating pin (305) comprises a central rod or conduit (308), typically a tube. Typically, the biasing member (306) comprises a spring, typically a helical spring. The helical spring may be made from any suitable alloy or polymer. The activating pin may also be made from a suitable alloy or polymer. The illustrated activator comprises an activating pin (305) surrounded by a substantially axially aligned helical spring (306), although other types of spring or biasing may be employed and are contemplated by the invention. Preferably, the activating pin (305) further comprises a circumferential flange (307). Typically, the biasing member (306) engages the circumferential flange (307).

The activating pin (305) further comprises an engagement member (309). The illustrated engagement member is in the form tubular protrusion from the circumferential flange. Typically, the engagement member (309) and the activating pin (305) form a unitary conduit. The engagement member is slidably engaged with the housing of the valve system (300). Preferably, all elements of the activator are slidably engaged with the housing of the valve system (300)

The valve system (300) further comprises a fluid connector (310) for engaging with an attachment member (not shown).

The valve system comprises an activator chamber (311) and a valve chamber (312). In use, the activator (304) is activated by applying an axial force to the activating pin (305). Typically, the axial force is applied to the distal end of the activating pin (305), preferably to the engagement member (369). In the illustrated embodiment, such an axial force causes the helical spring (307) to engage with a proximal inner wall (313) of the activator chamber (311). The helical spring is then compressed (307) and thereby exposes a proximal portion of the activating pin (305). The proximal end of the activating pin (305) engages with the one-way valve (302) and opens said valve. When the one-way valve (302) is open, fluid communication is provided between the fluid connector (310) and the fluid passageway (301). This may be either directly through the activating pin (305), if it is a conduit, or through the activator chamber (311) in alternative embodiments. As such, the inflatable portion of the medical device may be inflated.

Typically, attachment of said attachment member to said fluid connector activates said activator.

Typically, upon removal of the axial force to the activating pin (305) the activator (304) returns to its at rest, or deactivated, position. Typically, removal of the attachment member allows the biasing member (306) to return the activator (304) to its at rest position. In the illustrated embodiment, removal of the axial force allows the helical spring (306) to move the activating pin (305) in a distal direction until the circumferential flange (307) engages with a distal inner wall (314) of the activator chamber (311) or, at least, until the activating pin (305) is disengaged from the one-way valve (302), thereby allowing the one-way valve (302) to close.

The inflatable portion of the medical device may be inflated by passing fluid either through a conduit in the activating pin (305) or by passing said fluid around said circumferential flange (307).

The invention thereby enables the inflatable portion of the indwelling medical device to be inflated or deflated rapidly by way of said attachment member; preferably a syringe, more preferably a Luer tipped syringe. Once the device has been inflated, and the attachment member removed, the pressure within the inflatable portion is regulated by the one-way valve (302) and the compensator (303) of the valve system. When the pressure in the inflatable portion of the medical device is higher than atmospheric pressure, fluid will leave the valve system through the compensator (303). Whereas, when the pressure in the inflatable portion of the medical device is lower than atmospheric pressure, fluid will enter the valve system through the one-way valve (302) and/or the compensator (303).

It will be appreciated by those skilled in the art that the foregoing is a description of a preferred embodiment of the present invention and that variations in design and construction may be made to the preferred embodiment without departing from the scope of the invention as defined by the appended claims.

What is claimed is:

1. A valve system for an inflatable portion of an indwelling medical device comprising:
    a fluid passageway having a one-way valve associated therewith, said one-way valve being movable between an open position and a closed position, said open position permitting fluid to pass through said fluid passageway into the inflatable portion;
    a compensator associated with said fluid passageway, said compensator permitting fluid to enter or leave said fluid passageway in response to pressure changes within said passageway caused by pressure changes in the inflatable portion of the medical device when the one-way valve is in said closed position; and
    an activator for opening the one-way valve;
    wherein fluid is prevented from entering or leaving said fluid passageway through said compensator when the one-way valve is in said open position.

2. The valve system of claim 1, wherein the valve system further comprises a fluid connector associated with the activator.

3. The valve system of claim 1, wherein the activator is activated by applying an axial load.

4. The valve system of claim 2, wherein an attachment member is attached to the fluid connector.

5. The valve system of claim 4, wherein attachment of the attachment member to the fluid connector activates the activator.

6. The valve system of claim 1, wherein the activator comprises an activating pin and a biasing member.

7. The valve system of claim 6, wherein the biasing member is a helical spring.

8. The valve system of claim 6, wherein the activating pin comprises a conduit for providing fluid communication between a distal end and proximal end of the activating pin.

9. The valve system of claim 7, wherein the activating pin further comprises a circumferential flange.

10. The valve system of claim 9, wherein compression of the helical spring between the circumferential flange and a proximal end wall of an activator chamber upon activation of the activator exposes a proximal portion of the activating pin.

11. The valve system of claim 6, wherein the one-way valve is opened by the activator by engaging the activating pin.

12. The valve system of claim 6, wherein the one-way valve is a duck-bill valve, and the activating pin engages and opens the duck-bill valve.

13. The valve system of claim 1, wherein the activator is integrated with the fluid passageway.

14. The valve system of claim 1, wherein the activator is separate from the fluid passageway.

15. An indwelling medical device comprising an inflatable portion and a valve system of claim 1.

16. A rectal catheter or fecal management system comprising an inflatable portion and the valve system of claim 1.

17. The indwelling medical device of claim 15, wherein the inflatable portion comprises an open-cell foam.

18. The indwelling medical device of claim 17, wherein the foam is a polyurethane foam or a memory foam.

19. The indwelling medical device of claim 17, wherein the inflatable portion self-inflates.

20. A method for preparing an inflatable portion of an indwelling medical device for inflation or deflation comprising the steps of:
   a) providing a valve system according to claim 1; and
   b) attaching an attachment member thereto.

* * * * *